(12) United States Patent
Dorian et al.

(10) Patent No.: US 7,553,413 B2
(45) Date of Patent: Jun. 30, 2009

(54) PLASMA CONCENTRATOR DEVICE

(75) Inventors: Randel Dorian, San Diego, CA (US);
Michael D. Leach, Warsaw, IN (US);
Richard Wood Storrs, Berkeley, CA (US)

(73) Assignees: Hanuman LLC, San Francisco, CA (US); Biomet Biologics, LLC, Warsaw, IN (US)

( * ) Notice: Subject to any disclaimer, the term of this patent is extended or adjusted under 35 U.S.C. 154(b) by 546 days.

(21) Appl. No.: 11/342,982

(22) Filed: Jan. 30, 2006

(65) Prior Publication Data

US 2006/0175268 A1 Aug. 10, 2006

Related U.S. Application Data

(60) Provisional application No. 60/650,860, filed on Feb. 7, 2005.

(51) Int. Cl.
*B01D 15/02* (2006.01)
*B01D 24/00* (2006.01)
*B01D 29/00* (2006.01)

(52) U.S. Cl. ............... 210/219; 210/295; 210/502.1; 422/44; 422/102; 436/177; 436/178

(58) Field of Classification Search ............ 210/219, 210/295, 502.1; 422/44, 102; 436/177, 178
See application file for complete search history.

(56) References Cited

U.S. PATENT DOCUMENTS 3,723,244 A 3/1973 Breillatt, Jr.

(Continued)

FOREIGN PATENT DOCUMENTS

EP 0244834 11/1987

(Continued)

OTHER PUBLICATIONS

Fibrostik™ Plasma Concentrator, Attention Operating Surgeon, Cell Factor Technologies, Inc., Jul. 2003.

*Primary Examiner*—David A Reifsnyder
(74) *Attorney, Agent, or Firm*—Harness, Dickey

(57) ABSTRACT

A plasma concentrator of this invention having a concentrator chamber, concentrator gel beads, a filter, and an agitator. The agitator has agitator blades extending outwardly from the lower end. The agitator end is positioned in the concentrator chamber and supported for rotation about its central axis and for reciprocal movement along its central axis. The concentrator has a top with an upper opening through which the upper end of the actuator stem extends, and a lower opening in which the filter is positioned. The concentrator chamber can have a cylindrical inner wall, and the agitator blades can have an outer edge in close proximity to the inner wall with the space between the outer edge and the inner wall being less than the diameter of the gel beads. The filter is selected to block effective flow of plasma therethrough under ambient gravity conditions and permit plasma and plasma concentrate flow therethrough under centrifugal forces of the separation gravity. The method concentrates plasma by removing water without significantly denaturing the fibrinogen in the plasma. The plasma is introduced into a concentration chamber containing a plurality of dehydrated concentrator gel beads and an agitator. Then water is removed from the plasma while stirring the beads to reduce plasma polarization and breaking up clumps of beads that form during the agitation. Then centrifugal force can be applied to the concentrated plasma in an amount sufficient to separate a substantial portion of the plasma concentrate from the beads.

7 Claims, 4 Drawing Sheets

U.S. PATENT DOCUMENTS

| | | | |
|---|---|---|---|
| 3,931,010 A | 1/1976 | Ayres et al. | |
| 4,154,690 A | 5/1979 | Ballies et al. | |
| 4,379,849 A | 4/1983 | Heimreid et al. | |
| 4,714,457 A | 12/1987 | Alterbaum | |
| 5,376,263 A | 12/1994 | Fischel | |
| 5,501,371 A | 3/1996 | Schwartz-Feldman | |
| 5,560,830 A | 10/1996 | Coleman et al. | |
| 5,585,007 A | 12/1996 | Antanavich et al. | |
| 5,632,895 A | 5/1997 | Tsukagoshi et al. | |
| 5,632,905 A | 5/1997 | Haynes | |
| 5,733,466 A | 3/1998 | Benebo et al. | |
| 5,788,662 A | 8/1998 | Antanavich et al. | |
| 5,795,571 A | 8/1998 | Cederholm-Williams et al. | |
| 5,795,751 A | 8/1998 | Apel | |
| 5,934,803 A | 8/1999 | Hutter | |
| 5,958,253 A | 9/1999 | Holm et al. | |
| 6,027,655 A | 2/2000 | Holm et al. | |
| 6,063,297 A | 5/2000 | Antanavich et al. | |
| 6,214,338 B1 | 4/2001 | Antanavich et al. | |
| 6,274,090 B1 | 8/2001 | Coelho et al. | |
| 6,368,298 B1 | 4/2002 | Beretta et al. | |
| 6,417,004 B1 | 7/2002 | Brady et al. | |
| 6,444,228 B1 | 9/2002 | Baugh et al. | |
| 6,472,162 B1 | 10/2002 | Coelho et al. | |
| 6,516,953 B1 | 2/2003 | DiCesare et al. | |
| 6,596,180 B2 | 7/2003 | Baugh et al. | |
| 6,719,901 B2 | 4/2004 | Dolecek et al. | |
| 6,733,471 B1 | 5/2004 | Ericson et al. | |
| 6,905,612 B2 * | 6/2005 | Dorian et al. | 210/806 |
| 7,179,391 B2 | 2/2007 | Leach et al. | |
| 2002/0090711 A1 | 7/2002 | Karlsson | |
| 2002/0169408 A1 | 11/2002 | Beretta et al. | |
| 2002/0172666 A1 | 11/2002 | Sacchi et al. | |
| 2004/0120942 A1 | 6/2004 | McGinnis et al. | |
| 2004/0182795 A1 | 9/2004 | Dorian et al. | |
| 2005/0109716 A1 | 5/2005 | Leach et al. | |

FOREIGN PATENT DOCUMENTS

| | | |
|---|---|---|
| WO | WO-02/38610 | 5/2002 |
| WO | WO-02/060925 | 8/2002 |
| WO | WO-03/099412 | 12/2003 |
| WO | WO-2004/009207 | 1/2004 |

* cited by examiner

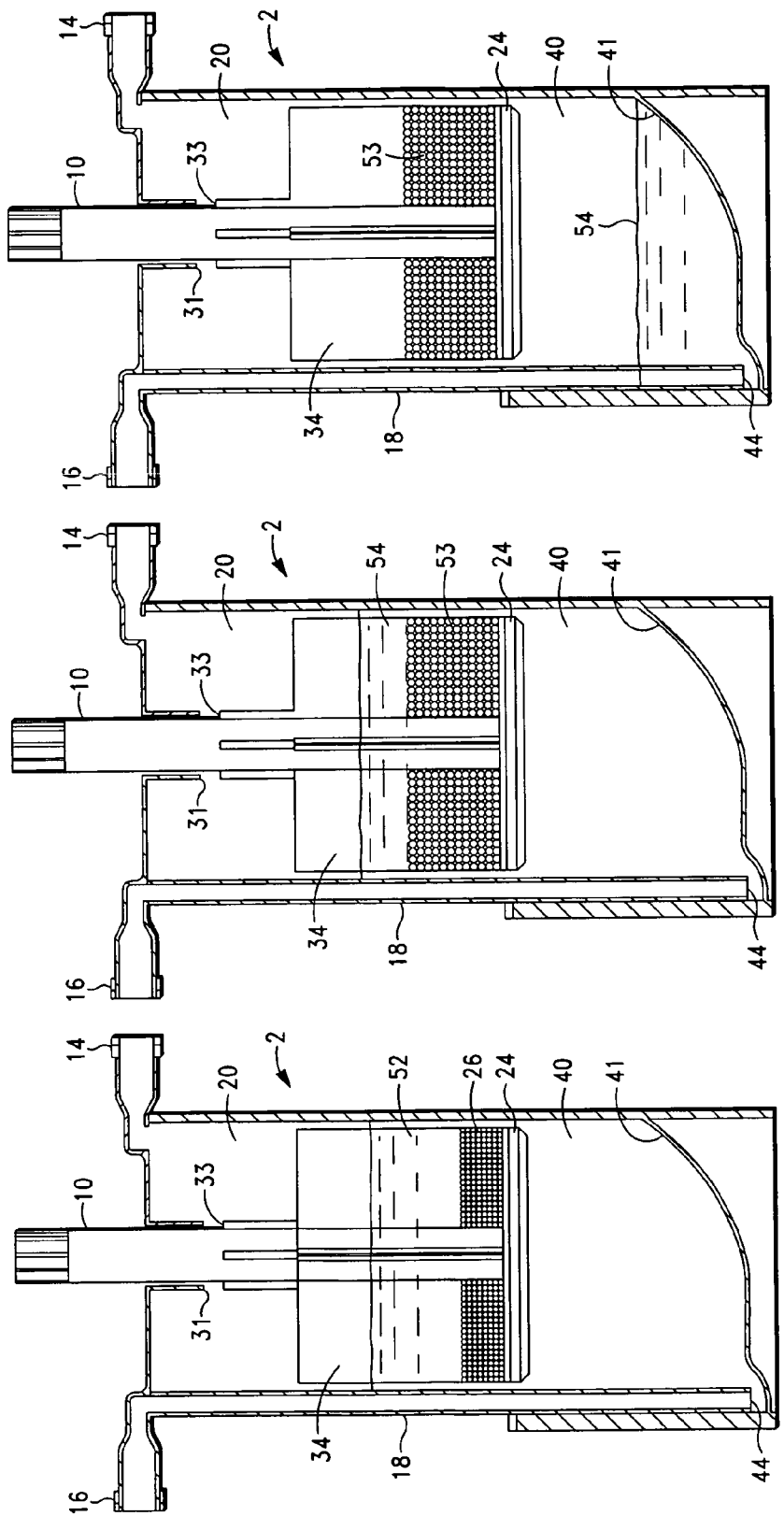

PLASMA CONCENTRATOR DEVICE

BENEFIT OF EARLIER FILING DATE UNDER 35 USC 120

This application claims the benefit under 35 USC 120 of the filing date of Provisional Application No. 60/650,860 filed Feb. 7, 2005.

FIELD OF THE INVENTION

This invention relates to an apparatus and method for preparing a plasma concentrate that can be used as a tissue sealant and a hemostat. Then plasma concentrate is preferably free of cells.

BACKGROUND OF THE INVENTION

Blood can be fractionated, and the different fractions of the blood can be used for different medical needs. Under the influence of gravity or centrifugal force, blood spontaneously sediments into three layers. At equilibrium, the top low-density layer is a straw-colored clear fluid called plasma. Plasma is a water solution of salts, metabolites, peptides, and many proteins ranging from small (insulin) to very large (complement components).

The bottom, high-density layer is a deep red viscous fluid comprising anuclear red blood cells (erythrocytes) specialized for oxygen transport. The red color is imparted by a high concentration of chelated iron or heme that is responsible for the erythrocytes' high specific gravity. The relative volume of whole blood that consists of erythrocytes is called the hematocrit, and in normal human beings this can range from about 37% to about 52% of whole blood.

The intermediate layer is the smallest, appearing as a thin white band above the erythrocyte layer and below the plasma layer; this is called the buffy coat. The buffy coat itself has two major components, nucleated leukocytes (white blood cells) and anuclear smaller bodies called platelets (or thrombocytes). Leukocytes confer immunity and contribute to debris scavenging. Platelets seal ruptures in blood vessels to stop bleeding, and deliver growth and wound healing factors to a wound site. Slower speed or shorter duration centrifugation permits separation of erythrocytes and leucocytes from plasma, while the smaller platelets remain suspended in the plasma, yielding platelet rich plasma (PRP).

A major improvement in making plasma concentrate from whole blood for use in wound healing and as a tissue sealant was described in U.S. Pat. No. 5,585,007; this patent is hereby incorporated by reference in its entirety. This device, designed for placement in a medical laboratory or surgical amphitheatre, with an integral centrifuge used a disposable cartridge for preparing tissue sealant. The device was particularly applicable for stat preparations of autologous tissue sealants. Preparation in the operating room of 5 ml of sealant from 50 ml of patient blood required less than 15 minutes and only one simple operator step. There was no risk of tracking error because processing can be done in the operating room. Chemicals added could be limited to anticoagulant (e.g., citrate) and calcium chloride. The disposable cartridge could fit in the palm of the hand and was hermetically sealed to eliminate possible exposure to patient blood and ensure sterility. Adhesive and tensile strengths of the product were comparable or superior to pooled blood fibrin sealants made with precipitation methods. Use of antifibrinolytic agents (such as aprotinin) was not necessary because the tissue sealant contained high concentrations of natural inhibitors of fibrinolysis from the patient's blood. This new tissue sealant also optionally contained patient platelets and additional factors that promote wound healing, healing factors that are not present in commercially available fibrin sealants.

The patented device used a new sterile disposable cartridge with the separation chambers for each run. Since the device was designed to be used in a normal medical setting with ample power, the permanent components, designed for long-term durability, safety and reliability, were relatively heavy, using conventional centrifuge motors and accessories.

Disposable plasma concentrating devices suitable for concentrating PRP according to this invention are described in commonly assigned, co-pending application Ser. No. 10/394,828 filed Mar. 21, 2003, now U.S. Pat. No. 6,905,612 B2, the entire contents of which are hereby incorporated by reference. The cell-free plasma fraction is removed and discarded.

SUMMARY OF THE INVENTION

The disposable device of this invention is suitable for preparing a highly valuable autologous plasma concentrate from cell-free plasma fractions.

The concentrating phase requires only simple manual manipulation (rotating the agitator shaft with reciprocal movement to disrupt gel bead clumping). The device is then spun with a conventional centrifuge to separate the plasma concentrate from the desiccated beads, moving the plasma concentrate from the concentrating zone into a plasma concentrate reservoir, from which it can be removed by a conventional applicator syringe.

The plasma concentrator of this invention comprises a concentrator chamber, a plurality of concentrator gel beads in the concentrator chamber, a filter, and an agitator. The agitator comprises an actuator stem having an upper agitator end and a lower agitator end, agitator blades extending outwardly from the lower end. The lower agitator end is positioned in the concentrator chamber, and mounted or supported for both rotation about its central axis and for reciprocal movement along its central axis. The concentrator has a top with an upper opening through which the upper end of the actuator stem extends, and a lower opening in which the filter is positioned. The concentrator chamber can have a cylindrical inner wall, and the agitator blades can have an outer edge in close proximity to the inner wall with the space between the outer edge and the inner wall being less than the diameter of the gel beads.

The upper opening of the concentrator can include a stop sleeve extending from the top of the concentrator into the concentrator chamber, the stop sleeve having a lower abutment surface. The agitator stem can have stop projections that extend outward beyond the diameter of the strop sleeve, the upper surfaces of the stop projections constituting abutment surfaces positioned to stop upward axial movement of the agitator when contacting the lower abutment surface of the stop sleeve.

The filter has an upper surface and the agitator blades can have a lower portion that contacts the upper surface of the filter and is positioned for sweeping the upper surface during rotation of the agitator and for making impact with the upper surface during downward movement of the agitator along its central axis. The downward motion of the blades during the reciprocal movement of the agitator can be arrested by abutment with the upper surface of the filter.

The filter is selected to block effective flow of plasma therethrough under ambient gravity conditions and permits plasma concentrate flow therethrough under centrifugal forces above 10 g's and up to at least as high as the separation gravity.

The plasma concentrator can be combined with a plasma concentrate outlet conduit and a plasma concentrate reservoir with an upper opening in communication with the filter and positioned to receive plasma concentrate passing through the filter. The plasma concentrator can have a sloping floor and a sump at the lowest end of the floor, one end of the plasma concentrate outlet conduit communicating with the sump.

The method of this invention for concentrating plasma by removing water without significantly denaturing the fibrinogen in the plasma can include introducing the plasma into a concentration chamber containing a plurality of dehydrated concentrator gel beads and an agitator. Then water is removed from the plasma until the plasma has a protein concentration greater than 1.5 times the protein concentration of the untreated plasma.

While the water is being removed, the agitator can be rotated to stir the beads to reduce plasma polarization and moved to break up clumps of beads that form during the agitation. Then centrifugal force can be applied to the concentrated plasma in an amount sufficient to separate a substantial portion of the plasma concentrate from the beads.

When the concentration chamber contains an agitator having agitator blades extending outwardly from its lower end, wherein the agitator is supported for rotation about its central axis and for reciprocal movement along its central axis, the agitator can be rotated to stir the beads while they are absorbing water from the plasma to reduce plasma polarization, and the agitator can be moved along its central axis in a reciprocal motion to break up clumps of beads that form during the agitation.

If the agitator blades rest on the upper surface of a filter, the agitator blades can have a lower portion that sweeps the upper surface of the filter during rotation, and impacts the upper surface of the filter during reciprocal motion of the agitator along its central axis. Then the agitator can be rotated to sweep the upper surface of the filter and stirring beads resting thereupon to reduce plasma polarization, and the agitator can be moved in a reciprocal motion to impact the upper surface of the filter and bead clumps forming on the surface during the stirring.

When the filter has pores that block effective flow of plasma therethrough under ambient gravity conditions and permits plasma and plasma concentrate therethrough at more than 10 g's and up to the separation gravity. The plasma can be maintained in contact with the beads by the filter during the water removal and plasma concentrate can be caused to flow through the filter when the mixture is subjected to centrifugal forces in the direction of the filter of as high as the separation gravity.

BRIEF DESCRIPTION OF THE DRAWINGS

FIG. 7 is a cross-sectional drawing of the plasma concentrating device shown in FIG. 3 after plasma has been introduced into the device.

FIG. 8 is a cross-sectional drawing of the plasma concentrating device shown in FIG. 7 after the gel beads have removed water from the plasma, swelling the beads.

FIG. 9 is a cross-sectional drawing of the plasma concentrating device shown in FIG. 8 after centrifuging, wherein the plasma concentrate has flowed into the plasma concentrate reservoir.

DETAILED DESCRIPTION OF THE INVENTION

The term "separation gravity" is a centrifugal force that is sufficient to separate plasma concentrate from the surface of the concentrator gel beads and to cause separated plasma concentrate to flow through the filter.

The device is one component of an improvement over the complex plasma separating and concentrating device described in U.S. Pat. No. 5,585,007. A simple, disposable device described in commonly assigned, copending application Ser. No. 10/394,828 filed Mar. 21, 2003, now U.S. Pat. No. 6,905,612 B2 rapidly separates plasma from blood using a conventional medical laboratory centrifuge. The device of this invention converts the plasma into an autologous concentrate highly useful as a tissue sealant and hemostat.

Figure 1:
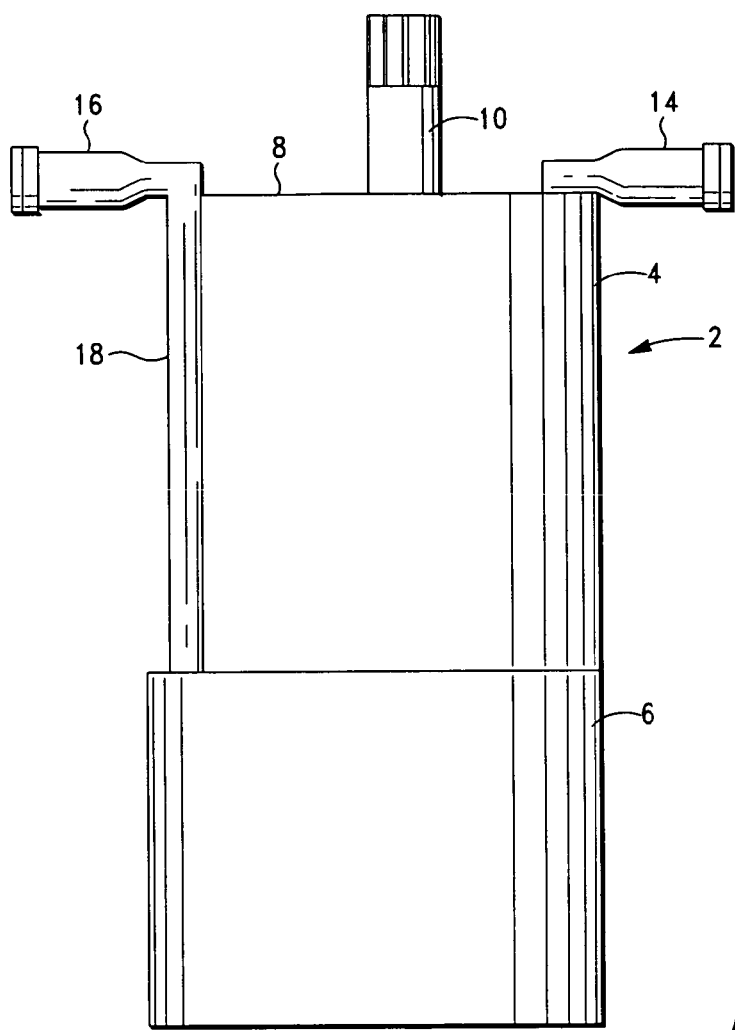
FIG. 1 is a front view of the plasma concentrating device of this invention.
Figure 2:
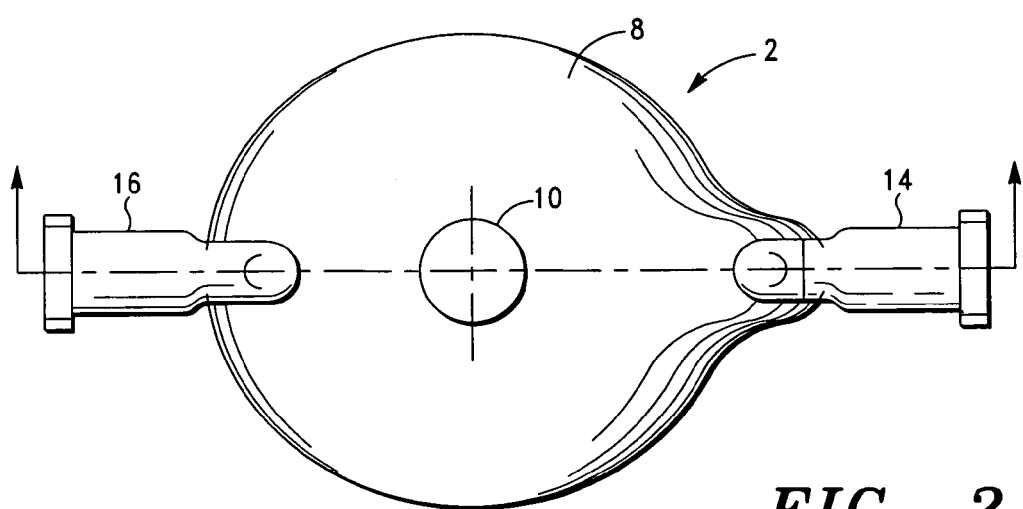
FIG. 2 is a top view of the plasma concentrating device shown in FIG. 1.

Referring to the drawings, FIG. 1 is a front view of the plasma concentrating device of this invention, and FIG. 2 is a top view of the plasma concentrating device shown in FIG. 1. This small compact device is suitable for processing up to 50 ml of plasma. The concentrator 2 has an upper concentrator housing 4 and a lower concentrate reservoir housing 6. The upper concentrator housing 4 has a top 8 through which the agitator stem 10 of a gel bead agitator 12 (See FIGS. 3-5) extends. The top 8 also has a plasma inlet port 14 that extends through the top 8 and communicates with the concentration chamber 20 (FIG. 3) enclosed by the upper concentrating housing 4. A plasma concentrate outlet port 16 communicates with a plasma concentrate conduit 18 shown in greater detail in FIG. 3.

Figure 3:
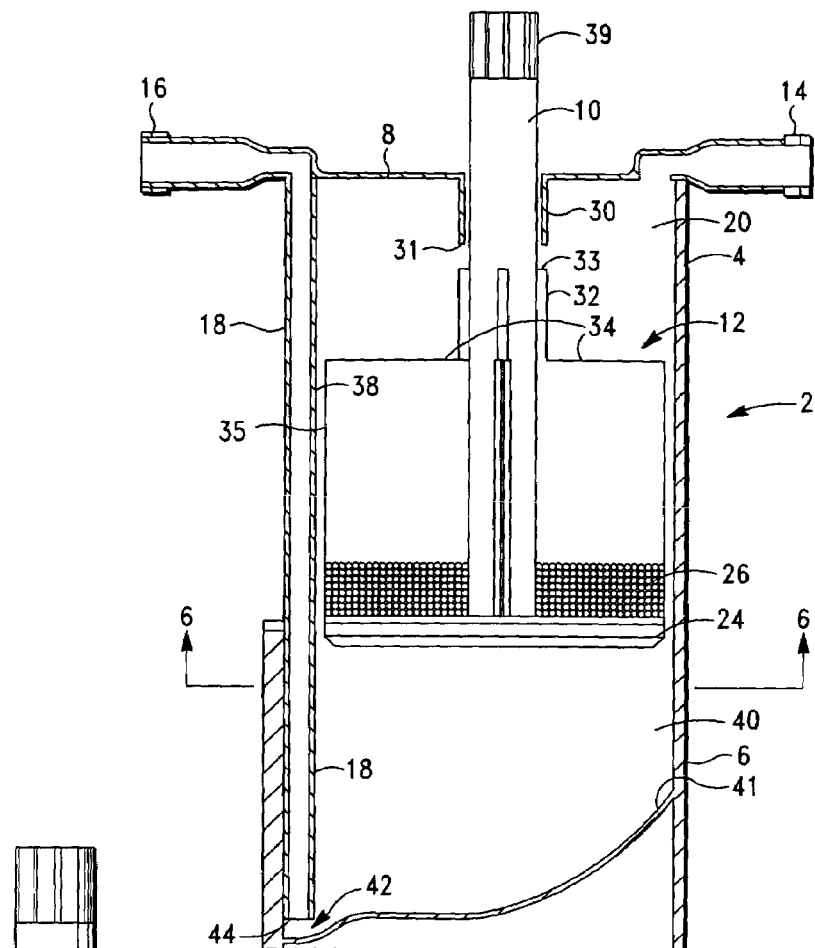
FIG. 3 is a cross-sectional drawing of the plasma concentrating device shown in FIG. 1 taken along the line 3-3 of FIG. 2.

FIG. 3 is a cross-sectional drawing of the plasma concentrating device shown in FIG. 1 taken along the line 3-3 of FIG. 2. FIG. 3 shows internal details of this device. The upper concentrator housing 4 encloses a concentrating chamber 20. The floor of the concentrating chamber 20 is filter 24, the upper surface of which supports desiccated concentrating gel beads 26.

The desiccated concentrating gel beads 26 can be insoluble beads or disks that will absorb a substantial volume of water and not introduce any undesirable contaminant into the plasma. They can be dextranomer or acrylamide hydrogel beads that are commercially available (Debrisan from Pharmacia and BIO-GEL P™ from Bio-Rad Laboratories, respectively). Alternatively, other concentrators can be used, such as SEPHADEX™ moisture or water absorbents (available from Pharmacia), silica gel, zeolites, cross-linked agarose, etc., in the form of insoluble inert beads. The beads are used in their desiccated state.

Gel bead agitator 12 is positioned with its bottom edge 28 resting on the top surface of filter base 24. Agitator stem 10 extends upward through a cylindrical stop sleeve 30 in the housing top 8. The stop sleeve 30 extends downward into the concentrating chamber 20 and service to support the agitator stem in a vertical orientation. The bottom edge surface 31 of the stop sleeve 30 constitutes a lower abutment surface. Integral projections 32 extend radially outward from the stirrer agitator stem 10 to a diameter larger than the inner diameter of the stop sleeve 30. The upper surfaces 33 of the projections 32 constitute upper abutment surfaces. As will be described in greater detail hereinafter, the gel bead agitator is rotated about its vertical axis and moved upward and downward in a reciprocal movement to stir the gel beads 26 during the water removal step. The contact of the low abutment edge 31 with the upper abutment surface 33 limits upward movement of the agitator blades or paddles 34 when they are raised during this reciprocal vertical movement of the stem 10.

Figure 4:
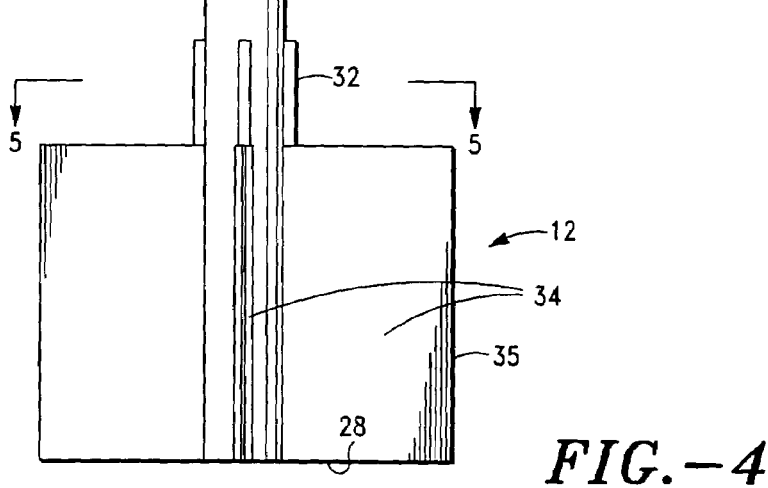
FIG. 4 is a front view of the agitator component of the plasma concentrating device of this invention.
Figure 5:
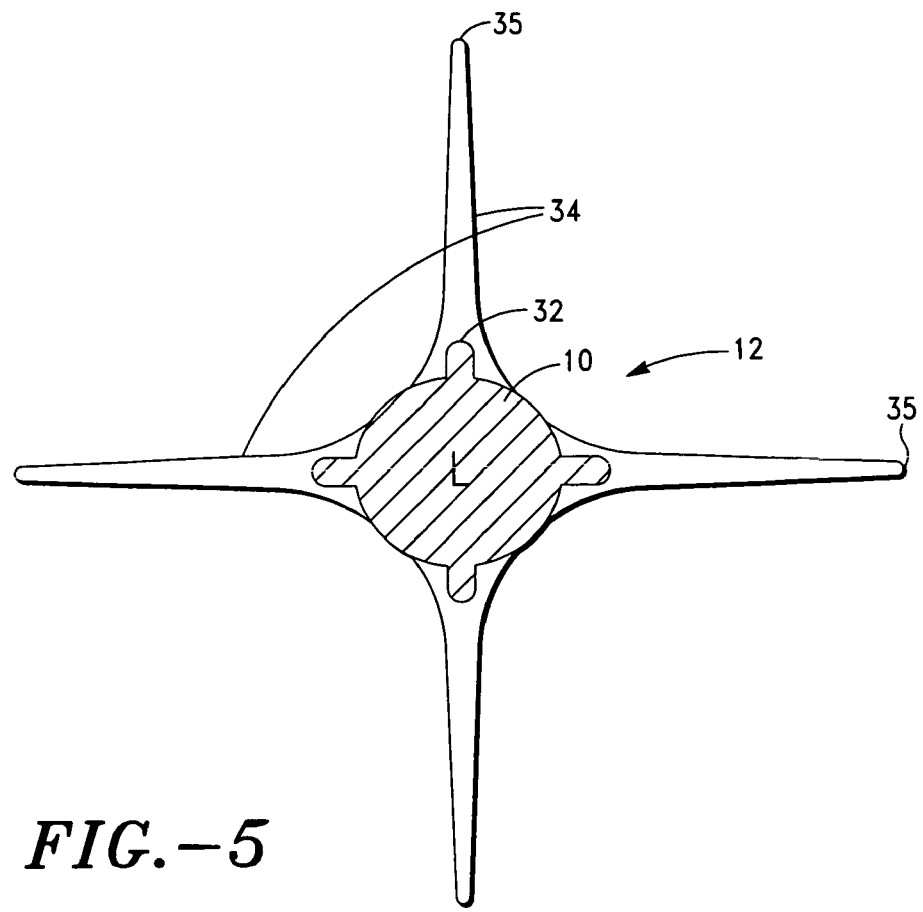
FIG. 5 is cross-sectional view of the agitator component show in FIG. 4, taken along the line 5-5.

Referring to FIGS. 3-5, the agitator comprises a plurality of paddles blades 34 extending radially outwardly from the central chamber stem 41. The outer vertical edge of the agitator blades are sized to make a sliding engagement with the inner surface 38 of the chamber housing 4 (FIG. 3). The distance between the outer edge of the paddles 34 and the inner surface 38 of the chamber housing should be smaller than the diameter of the individual gel beads to prevent individual gel beads from wedging between the agitator and the wall surface. Rotation of stem 10 about its central axis rotates the paddles 34 and stirs the beads 26.

FIG. 4 is a front view of the agitator component of the plasma concentrating device of this invention, and FIG. 5 is cross-sectional view of the agitator component show in FIG. 4, taken along the line 5-5.

The upper end of the stem 10 can optionally have a plurality of splines 39 that can mate with an optional agitator handle (not shown) or that can function as friction surfaces, facilitating manual rotation of the stem.

Referring to FIG. 3, the lower concentrate chamber housing 6 encloses a concentrate chamber 40 with a sloped bottom 41 leading to a sump or depression 42. The concentrate conduit 18 has a conduit end 44 that extends into the depression 42 to draw in most of the liquid concentrate (not shown) through the concentrate outlet 16 when the pressure in the conduit 18 is reduced.

Figure 6:
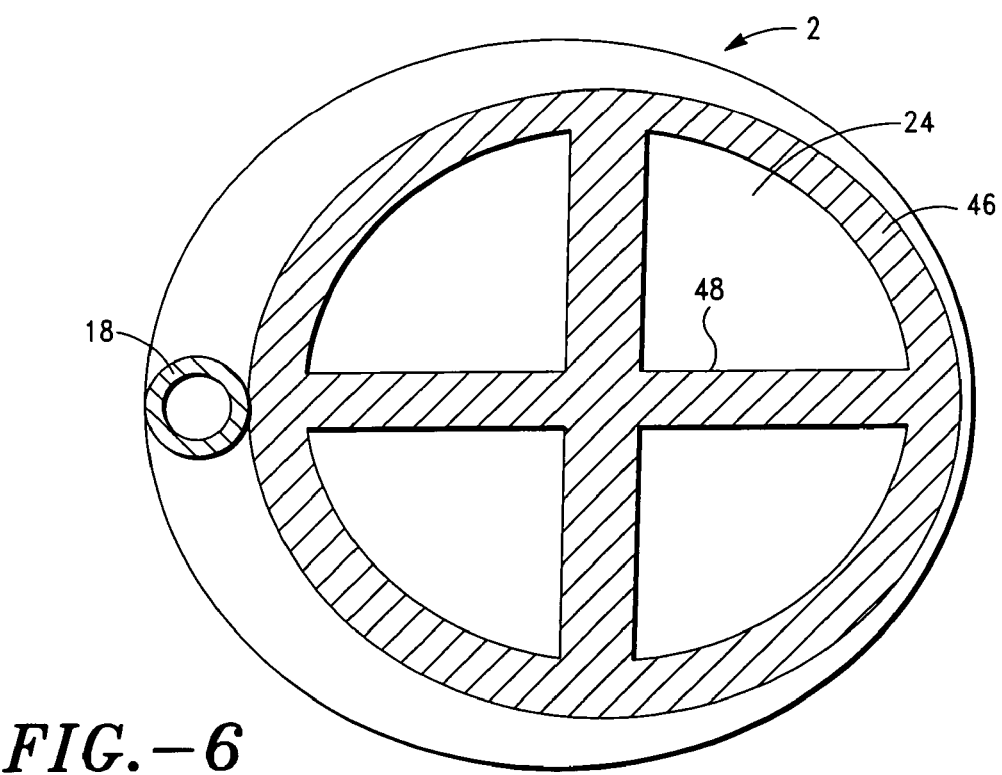
FIG. 6 is a cross-sectional drawing of the plasma concentrating device shown in FIG. 3, taken along the line 6-6.

The construction and function of the filter 24 is described in greater detail with respect to FIG. 6. FIG. 6 is a cross-sectional drawing of the plasma concentrating device shown in FIG. 3, taken along the line 6-6.

The filter 24 is supported by a flat circular ring 46 and flat radial spokes 48. The openings in the support are designed to permit liquid flow through the filter under the pressure of centrifugal force. The filter must retain the plasma above the filter under ambient gravity during the water removal phase and permit plasma concentrate flow therethrough at centrifugal pressures used in the separation. Therefore the filter should retain fluid for at least up to 10 g's and permit flow at the separation gravity. The separation gravity is created when the system is spun in a centrifuge, the centrifugal force being directed in the axial direction through the filter. The higher the centrifugal force applied is during the plasma concentrate separation, the more effective the recovery of the plasma concentrate.

The concentration process has as its critical objective, the removal of water from the plasma without significantly denaturing the fibrinogen component of the plasma. This component provides effective the clotting action of blood and provides the sealing, adhesive and homeostatic properties of the concentrate.

The process is illustrated in FIGS. 7-9 wherein FIG. 7 is a cross-sectional drawing of the plasma concentrating device shown in FIG. 3 after plasma has been introduced into the device; FIG. 8 is a cross-sectional drawing of the plasma concentrating device shown in FIG. 7 after the gel beads have removed water from the plasma, swelling the beads; and FIG. 9 is a cross-sectional drawing of the plasma concentrating device shown in FIG. 8 after centrifuging, wherein the plasma concentrate has flowed into the plasma concentrate reservoir.

In the first step of the process, blood plasma 52 (preferably cell free) is introduced into the concentrating chamber 20 through the plasma inlet port 14. The plasma 52 entering the chamber 20 flows to the bottom of the chamber where it contacts the gel beads 26 as shown in FIG. 7.

As the gel beads 26 remove water from the plasma, the plasma contacting each bead's surface thickens, creating gel polarization that it impedes water absorption by the bead. Furthermore, as the thickened plasma becomes more viscous, the beads tend to clump. To disrupt the thickened plasma layer forming on each bead, the agitator stem 10 is rotated around its central axis, moving the agitator blades 34 through the beads and stirring the beads. To break up bead clumps, the agitator blades 34 can be raised and lowered by reciprocal motion of the agitator stem 10 along its central axis, the bottom edges 28 of the blades (FIG. 3) impact the bead clumps against the filter surface disrupting the clumps. The vertical movement of the agitator blades is limited to a range established by the upper surface of the filter 24 range of movement is defined by the floor 4 of the chamber and impingement contact between the abutments 31 and 33. The water swollen beads 53 and the concentrated plasma 54 are shown in FIG. 8. During this concentration stage, the plasma and its components can be concentrated to a concentration of from 1.5-3 times or higher than its original concentration.

The device of this invention is then placed in the cup receptors of a conventional laboratory centrifuge (not shown) and spun at a speed that will create a separation gravity, that is, a centrifugal force that will remove plasmas concentrate from the surface of the gel beads, and cause the plasma concentrate to flow through the filter. The filter can be constructed to allow flow of liquid therethrough at pressures above 10 g's. The centrifugal pressure forces of the plasma concentrate to flow from the bead surface through the filter 24 and into the plasma concentrate reservoir 40. The higher the centrifugal force applied, the more effective will be the stripping of the plasma concentrate from the surface of the gel beads. After centrifugation is completed, the device is removed from the centrifuge.

FIG. 9 shows the device with the plasma concentrate in the reservoir. The plasma concentrate is then drawn from the plasma concentrate reservoir through conduit to the plasma concentrate outlet.

The invention claimed is:

1. A plasma concentrator comprising a concentrator chamber, a plurality of concentrator gel beads in the concentrator chamber, a filter, and an agitator, the agitator comprising an actuator stem having an upper agitator end and a lower agitator end, agitator blades extending outwardly from the lower end, the lower agitator end being positioned in the concentrator chamber and supported for rotation about its central axis and for reciprocal movement along its central axis, and the concentrator having a top with an upper opening through which the upper end of the actuator stem extends, and a lower opening in which the filter is positioned.

2. The plasma concentrator of claim 1 wherein the concentrator chamber has a cylindrical inner wall, agitator blades having an outer edge in close proximity to the inner wall with the space between the outer edge and the inner wall being less than the diameter of the gel beads.

3. The plasma concentrator of claim 1 wherein the upper opening of the concentrator includes a stop sleeve extending from the top of the concentrator into the concentrator chamber, the stop sleeve having a lower abutment surface, and the agitator stem has stop projections that extend outward beyond the diameter of the strop sleeve, the upper surfaces of the stop projections constituting abutment surfaces positioned to stop upward axial movement of the agitator when contacting the lower abutment surface of the stop sleeve.

4. The plasma concentrator of claim 3 wherein the filter has an upper surface and the agitator blades have a lower portion that contacts the upper surface of the filter and is positioned for sweeping the upper surface during rotation of the agitator and for making impact with the upper surface during downward movement of the agitator along its central axis, the downward motion of the blades during the reciprocal movement of the agitator being arrested by abutment with the upper surface of the filter.

5. The plasma concentrator of claim 1 wherein the filter blocks effective flow of plasma therethrough under ambient gravity conditions and permits free plasma concentrate flow therethrough under centrifugal forces at the separation gravity.

6. The plasma concentrator of claim 5 wherein the separation gravity is greater than 10 g's.

7. The plasma concentrator of claim 1 wherein the plasma concentrator is combined with a plasma concentrate outlet conduit and a plasma concentrate reservoir with an upper opening in communication with the filter and positioned to receive plasma concentrate passing through the filter, the plasma concentrator having a sloping floor and a sump at the lowest end of the floor, one end of the plasma concentrate outlet conduit communicating with the sump.

* * * * *

UNITED STATES PATENT AND TRADEMARK OFFICE
CERTIFICATE OF CORRECTION

PATENT NO. : 7,553,413 B2  Page 1 of 1
APPLICATION NO. : 11/342982
DATED : June 30, 2009
INVENTOR(S) : Randel Dorian et al.

It is certified that error appears in the above-identified patent and that said Letters Patent is hereby corrected as shown below:

In column 1, line 44; delete "leucocytes" insert --leukocytes--

In column 2, line 53; delete "strop" insert --stop--

In column 5, line 13; delete "paddles" insert --paddle--

In column 6, line 32; delete "plasmas" insert --plasma--

In column 6, line 33; insert a space between "beads," and "and"

In column 7, line 4; delete "strop" insert --stop--

Signed and Sealed this

Eighteenth Day of August, 2009

David J. Kappos
*Director of the United States Patent and Trademark Office*